(12) United States Patent
Wakefield et al.

(10) Patent No.: US 7,470,539 B2
(45) Date of Patent: *Dec. 30, 2008

(54) FORMATION OF POLYAMPHOLYTES IN THE PRESENCE OF A POLYION

(75) Inventors: Darren H. Wakefield, Fitchburg, WI (US); David B. Rozema, Madison, WI (US); Jon A. Wolff, Madison, WI (US); Vladimir Trubetskoy, Middleton, WI (US); James E. Hagstrom, Middleton, WI (US); Vladimir G. Budker, Middleton, WI (US); Jason Klein, Madison, WI (US); So Wong, Oregon, WI (US)

(73) Assignee: Roche Madison Inc.

( * ) Notice: Subject to any disclaimer, the term of this patent is extended or adjusted under 35 U.S.C. 154(b) by 356 days.

This patent is subject to a terminal disclaimer.

(21) Appl. No.: 11/256,322

(22) Filed: Oct. 21, 2005

(65) Prior Publication Data

US 2006/0063257 A1  Mar. 23, 2006

Related U.S. Application Data

(60) Division of application No. 11/046,598, filed on Jan. 28, 2005, now Pat. No. 7,094,605, which is a continuation-in-part of application No. 10/095,752, filed on Mar. 11, 2002, now Pat. No. 6,881,576, which is a continuation-in-part of application No. 09/753,990, filed on Jan. 2, 2001, now Pat. No. 6,383,811.

(60) Provisional application No. 60/647,293, filed on Jan. 26, 2005.

(51) Int. Cl.
 *C12N 15/88* (2006.01)
(52) U.S. Cl. .................. 435/458; 435/320.1; 424/450; 536/23.1
(58) Field of Classification Search ....................... None
 See application file for complete search history.

(56) References Cited

U.S. PATENT DOCUMENTS

| 7,094,605 | B2 * | 8/2006 | Wakefield et al. ........... 435/458 |
| 2001/0044412 | A1 | 11/2001 | Wolff et al. |
| 2003/0220289 | A1 | 11/2003 | Monahan et al. |
| 2003/0224055 | A1 | 12/2003 | Lowlo et al. |

* cited by examiner

*Primary Examiner*—James S Ketter
(74) *Attorney, Agent, or Firm*—Kirk Ekena; Mark K. Johnson

(57) ABSTRACT

Polyampholyte are able to condense nucleic acid to form small complexes which can be utilized in the delivery of nucleic acid to mammalian cells. The polyampholytes can be formed prior to interaction with nucleic acid or they can be formed in the presence of nucleic acid. Stabilized polycation/nucleic acid complexes can be modified to reduce the positive charge of the polycation and add targeting ligands without destabilizing the complex. The resultant particles retain their small size and are more effective in delivery of nucleic acid to cells in vivo.

17 Claims, 3 Drawing Sheets

Effect of amount of activated SPLL on surface charge of DNA/PLL complexes

FORMATION OF POLYAMPHOLYTES IN THE PRESENCE OF A POLYION

CROSS-REFERENCE TO RELATED APPLICATIONS

This application is a divisional of application Ser. No. 11/046,598, filed Jan. 28, 2005 now U.S. Pat. No. 7,094,605, allowed, which is a continuation-in-part of application Ser. No. 10/095,752, filed Mar. 11, 2002 now U.S. Pat. No. 6,881,576, which is a continuation-in-part of application Ser. No. 09/753,990 filed on Jan. 2, 2001 now U.S. Pat. No. 6,383,811. This application also claims the benefit of U.S. Provisional Application No. 60/647,293, filed Jan. 26, 2005.

FIELD OF THE INVENTION

In this specification we describe forming a polyampholyte in the presence of polyion. The polyampholyte is useful in delivering a polyion to a cell. More specifically, the polyion may be a nucleic acid in a preferred embodiment.

BACKGROUND OF THE INVENTION

Low molecular weight cations with valency, i.e. charge, <+3 fail to condense DNA in aqueous solutions under normal conditions. However, cationic molecules with the charge <+3 can be polymerized in the presence of DNA and the resulting polymers can cause DNA to condense into compact structures. Such an approach is known in synthetic polymer chemistry as template polymerization. During this process, monomers (which are initially weakly associated with the template) are positioned along template's backbone, thereby promoting their polymerization. Weak electrostatic association of the nascent polymer and the template becomes stronger with chain growth of the polymer. Trubetskoy et al used two types of polymerization reactions to achieve DNA condensation: step polymerization and chain polymerization (Trubetskoy V S et al. 1998). Bis(2-aminoethyl)-1,3-propanediamine (AEPD), a tetramine with 2.5 positive charges per molecule at pH 8 was polymerized in the presence of plasmid DNA using cleavable disulfide amino-reactive cross-linkers dithiobis (succinimidyl propionate) and dimethyl-3,3'-dithiobispropionimidate. Both reactions yielded DNA/polymer complexes with significant retardation in agarose electrophoresis gels demonstrating significant binding and DNA condensation. Treatment of the polymerized complexes with 100 mM dithiothreitol (DTT) resulted in the pDNA returning to its normal supercoiled position following electrophoresis proving thus cleavage the backbone of the. The template dependent polymerization process was also tested using a 14 mer peptide encoding the nuclear localizing signal (NLS) of SV40 T antigen as a cationic "macromonomer". Other studies included pegylated comonomer (PEG-AEPD) into the reaction mixture and resulted in "worm"-like structures (as judged by transmission electron microscopy) that have previously been observed with DNA complexes formed from block co-polymers of polylysine and PEG (Wolfert M A et al. 1996). Blessing et al. (1998) used bisthiol derivative of spermine and reaction of thiol-disulfide exchange to promote chain growth. The presence of DNA accelerated the polymerization reaction as measured the rate of disappearance of free thiols in the reaction mixture.

Caging of Polycation-Condensed DNA Particles:

The stability of DNA nanoassemblies based on DNA condensation is generally low in vivo because they easily engage in polyion exchange reactions with strong polyanions. The process of exchange consists of two stages: 1) rapid formation of a triple DNA-polycation-polyanion complex, 2) slow substitution of one same-charge polyion with another. At equilibrium conditions, the whole process eventually results in formation of a new binary complex and an excess of a third polyion. The presence of low molecular weight salt can greatly accelerate such exchange reactions, which often result in complete disassembly of condensed DNA particles. Hence, it is desirable to obtain more colloidally stable structures where DNA would stay in its condensed form in complex with corresponding polycation independently of environment conditions.

The complete DNA condensation upon neutralization of only 90% of the polymer's phosphates results in the presence of unpaired positive charges in the DNA particles. If the polycation contains such reactive groups, such as primary amines, these unpaired positive charges may be modified. This modification allows practically limitless possibilities of modulating colloidal properties of DNA particles via chemical modifications of the complex. We have demonstrated the utility of such reactions using traditional DNA-poly-L-lysine (DNA/PLL) system reacted with the cleavable cross-linking reagent dimethyl-3,3'-dithiobispropionimidate (DTBP) which reacts with primary amino groups with formation of amidines. Similar results were achieved with other polycations including poly(allylamine) and histone H1. The use of another bifunctional reagent, glutaraldehyde, has been described for stabilization of DNA complexes with cationic peptide CWK18 (Adami R C et al. 1999).

Recharging:

The caging approach described above could lead to more colloidally stable DNA assemblies. However, this approach may not change the particle surface charge. Caging with bifunctional reagents, which preserve positive charge of amino group, keeps the particle positive. However, negative surface charge would be more desirable for many practical applications, i.e. in vivo delivery. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, changing the surface charge to opposite one. This whole process is salt dependent with flocculation to occur upon reaching the neutralization point.

We have demonstrated that similar layering of polyelectrolytes can be achieved on the surface of DNA/polycation particles (Trubetskoy V S et al. 1999). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex using a new DNA condensation assay (Trubetskoy VS et al. 1999b) and static light scattering. It has been found that certain polyanions such as poly(methacrylic acid) and poly (aspartic acid) decondensed DNA in DNA/PLL complexes. Surprisingly, polyanions of lower charge density such as succinylated PLL and poly(glutamic acid), even when added in 20-fold charge excess to condensing polycation (PLL) did not decondense DNA in DNA/PLL (1:3) complexes. Further studies have found that displacement effects are salt-dependent. In addition, poly-L-glutamic acid but not the relatively weaker polyanion succinylated poly-L-lysine (SPLL) displaces DNA at higher sodium chloride concentrations. Measurement of zeta-potential (ξ-potential) of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact.

The polyanion can be covalently attached to the polycation using a variety of chemical reactions without the use of crosslinkers. The polyanion can contain reactive groups that covalently attach to groups on the polycation. A preferable situation includes formation of a specific complex between a polyanion and a polycation, leaving the polyion and the polyampholyte to non-covalently interact electrostatically. The utility of such complexes includes enhanced colloid stability in serum and in high salt solutions and delivery of polyion (DNA) to hepatocytes in vivo upon intravenous administration.

SUMMARY OF THE INVENTION

In a preferred embodiment, we describe a process for forming nucleic acid complexes that can be delivered to cells comprising: condensing nucleic acid with a polycation, crosslinking the polycation to stabilize the complex and chemically modifying positively charged moieties on the polycation to reduce the surface charge of the particle. Reducing the charge of polycation-nucleic acid complexes reduces undesirable effects frequently associated with positively charge particles delivered in vivo.

In a preferred embodiment, a process is described for delivering a nucleic acid to a cell, comprising, forming a compound having a net charge comprising nucleic acid and polycation in a solution, adding a multifunctional crosslinking reagent, adding a polymer-reactive agent to form a complex having a net charge less positively charged than the compound net charge, and inserting the complex into a mammal.

In a preferred embodiment, the polycation condensed DNA particle is caged by addition of a multifunctional crosslinking reagent. The crosslinking reagent can be a homofunctional crosslinker or a heterofunctional crosslinker. A preferred crosslinker is a bifunctional crosslinking reagent. The crosslinker can contain a labile bond. The labile bond may be broken upon exposure to an acidic pH environment, a change in redox potential, cellular enzymes, cellular compounds, such as but not limited to glutathione, or a co-delivered or subsequently delivered reagent. The crosslinker can increase the positive surface charge of the polycation-nucleic acid complex, reduced the positive surface charge of the polycation-nucleic acid complex, or be chosen such that it does not effect the surface charge of the polycation-nucleic acid complex. In a preferred embodiment, the crosslinker forms covalent linkages to amines on the polycation but does not completely knock out the positive charge associated with the amines.

In a preferred embodiment, the positive surface charge of a polycation-nucleic acid complex is reduced by chemically modifying positively charge moieties on the polycation after formation of the complex. Prior to neutralization of charge on the polycation, the complex is stabilized by crosslinking. The surface chare of the complex is reduced through modification of the polymer by the cation-reactive reagents. The cation-reactive reagents chemically modify positively charged groups or moieties on the polycation. The modification can be reversible or labile. The cation reactive reagent may be neutral or negatively charged. The cation-reactive reagent can contain a labile bond or from a labile bond with the polycation. The labile bond may be broken upon exposure to an acidic pH environment, cellular enzymes, cellular compounds, such as but not limited to glutathione, or a co-delivered or subsequently delivered reagent. Upon modification of the complex, the surface charge, or zeta potential, of the complex may be less positively charged than the unmodified complex, charge neutral, or negatively charged.

In a preferred embodiment, the cation-reactive reagents that reduce the measured zeta potential of the particle may contain an interaction modifier. A preferred interaction modifier consists of polyethylene glycol. In another preferred embodiment, the cation-reactive reagents that reduce the measured zeta potential of the particle are acid-labile maleic anhydride derivatives.

In another preferred embodiment a targeting ligand may be attached to the particle either before or after the reduction of the particle's zeta potential.

Further objects, features, and advantages of the invention will be apparent from the following detailed description when taken in conjunction with the accompanying drawings.

DETAILED DESCRIPTION OF THE INVENTION

Figure 1:
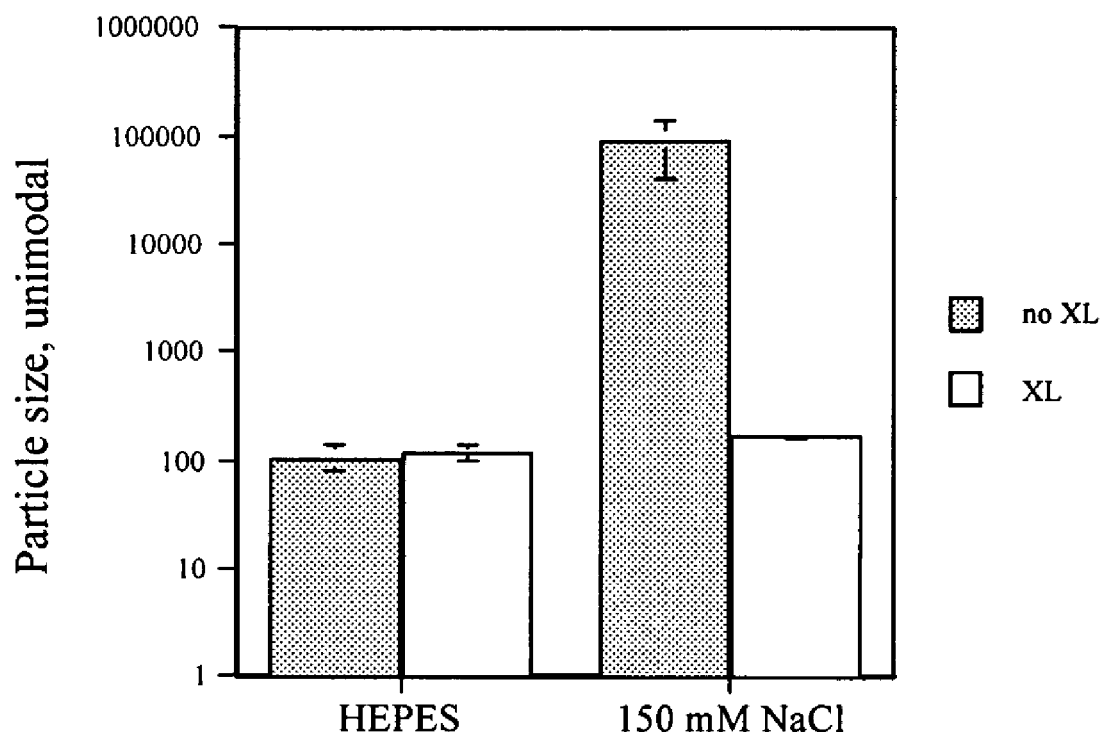
FIG. 1. Illustration of salt stability for cross-linked and non-crosslinked DNA/PLL/SPLL particles.

We show that it is possible to chemically reduce that charge of polycation/DNA particles while maintaining the stability and size of the particles. This chemical charge neutralization improves the ability of polycation condensed nucleic acid to be targeted to cells in vivo.

Modifying the Surface Charge of Nucleic Acids Complexes:

DNA particles condensed with an excess of cation have a positive zeta potential, which is the difference in the charge between the layer of ions surrounding the particle and the charge of the bulk fluid surrounding this particle. The zeta potential is usually measured in millivolts. As a result of a positive zeta potential such condensed DNA particles interact nonspecifically with cells, and extracellular components such as serum proteins (Wolfert et al. 1996, Dash et al. 1999, Plank et al. 1996, Ogris et al. 1999).

The most common method to reduce nonspecific interactions is the attachment of polyethylene glycol (PEGylation) or similar hydrophilic polymer to the condensing polycation. PEGylation does result in increased circulation times for DNA particles. However, the extent of PEGylation is limited in that PEGylation decreases the strength of the interaction between DNA and polycation. In addition, PEGylation does not prevent the displacement of DNA by polyanions (Mannisto Vanderkerken et al. 2002).

A method to prevent displacement of DNA by polyanion is caging, or cross-linking, which is linking of two moieties of a polymer or polymers to one another using a multifunctional chemical linker. As a result the polymer, as a network, becomes stronger and more resistant to being dissolved. Covalent linking bifunctional linkers may be homobifunctional (which involves the same chemical reaction for linking both moieties) or heterobifunctional (involves two different reactions allowing linkage of different functional groups). By cross-linking, a cage may be formed around or near the polyion creating a more stable complex of polyion and polymer. Cross-linking the polymer protects the polyion from being destroyed by enzymes and other degrading substrates. In addition, the DNA is resistant to displacement by polyanions.

We show that the stability of the caged DNA particle enables one to modify the particle with reagents that reduce its zeta potential by reducing the basicity of the constituent charged groups of the polycation, thereby reducing the charge of the polycation at neutral pH. For example, acylation of an amine-containing polycation reduces the charge of the polymer by forming amide groups that have a greatly reduced pKa. In this way, the zeta potential of a DNA particle may be controlled. Examples of acylation reagents include activated esters, e.g. N-hydroxy succinimide esters, and anhydrides.

We demonstrate that small, salt stable DNA/polycation complexes with reduced surface charge (zeta potential) can be formed by condensing the DNA with a polycation, crosslinking the polycation and subsequently modifying the polycation in the complex with cation-reactive reagents that reduced the measured zeta potential of the complex. The crosslinking reagent may contain a pH or redox labile bond. The cation-reactive reagents, which reduce the surface charge of the complex, may contain polyethylene glycol or a similar hydrophilic polymer. The cation-reactive reagent may form an acid-labile modification of the polymer. Such a cation-reactive agent may be, but is not limited to, a maleic anhydride derivative. The cation-reactive reagent may be negatively charged. A targeting ligand may also be attached to the complex.

Template polymerizations can be defined as polymerizations in which polymer chains are able to grow along template macromolecules for the greater part of their lifetime (van de Grampel H T et al. 1990). Such a mode of propagation can be achieved through the existence of cooperative interactions between the growing chain and the template chain and usually leads to the formation of an interpolymer complex. In general, a well-chosen template is able to affect the rate of polymerization as well as the molecular weight and microstructure of the formed polymer (daughter polymer). The concepts of template polymerization were described by Ballard and Bamford with the ring opening polymerization of the N-carboxyanhydride of DL-phenylalanine on a polysarcosine template. Since then, many other systems involving radical and non-radical initiation of vinyl monomers have been studied in which one or more template effects, arising from this peculiar propagation mode, were identified. A number of radical-initiated template polymerizations have been studied, employing water as solvent.

The main features of template polymerization are:
1. Complex formation takes place between polymers
2. The rate of polymerization increases as the concentration of template increases. (Fujimori K 1979)
3. The structure and conformational features of the template are reflected in the corresponding daughter polymer.

In template polymerization, propagation of new polymer chain occurs predominantly along the template, a macromolecular chain, through specific cooperative interaction. The nature of interaction can be electrostatic, H-bonding, charge-transfer, and Van der Waals forces in combination with stereochemical matching. The presence of template usually affects various polymerization characteristics as well as the microstructure of the polymer formed. The mechanism of template polymerization depends on the degree of monomer adsorption. Two extreme cases can be discerned: the adsorption equilibrium constant for monomer, $K_M=\infty$ (type 1) and $K_M=0$ (type 2). In type 1 ("zip" reaction) monomer is fully adsorbed onto all template sites and the polymerization occurs only on template. As the $K_M$ constant becomes smaller, template propagation increasingly proceeds via reaction monomers from the surrounding solution at the expense of reaction with adjacently adsorbed monomer. When $K_M=0$ (type 2) only non-adsorbed monomer is present and the template macromolecules are completely solvated by solvents instead of the monomers. A prerequisite for template propagation under this condition is the growing daughter oligomer, created in bulk solution, that then complexes with template. ("pick-up" reaction). The chain length below which no complexation takes place (critical chain length) is important for magnitude of the template effect. In fact, there is no sharp border between type 1 and type 2 polymerizations.

Several processes for using template polymerization for drug delivery are described. The daughter polymer could be the drug. In a preferred embodiment, the template is the drug (defined to include pharmaceuticals, therapeutic agents or biologically active substances). The process of using template polymerization for drug delivery comprises mixing the template with monomers and having a daughter polymer forming from the monomers. The mixture of template polymer and daughter polymer is then administered to a cell by putting the mixture in contact with a cell or near a cell. The mixture of template and daughter polymer could also be placed in a pharmaceutical formulation and vial for delivery to an animal. The template polymer could be a polyanion such as nucleic acid including DNA, RNA or an antisense sequence.

After template polymerization networks or additional networks can be added to the polymer. These could be used to cross-link the polymers. For example, the polymer could be cross-linked to "cage" the template. Also targeting groups can be added during the initial template polymerization stage or during subsequent polymerization steps.

DEFINITIONS

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups. Monomers can also be intercalating agents such as acridine, thiazole organge, or ethidium bromide.

Polymers can have other groups that increase their utility. These groups can be incorporated into monomers prior to polymer formation or attached to the polymer after its formation. These groups may contain main chain atoms, side chain atoms, polymer terminating atoms, or a combination of these. Functional groups include cell targeting signals, nuclear localization signals, compounds that enhance release of contents from endosomes or other intracellular vesicles (releasing signals), and other compounds that alter the behavior or interactions of the compound or complex to which they are attached. These groups (or moieties) can be covalently linked to a polycation in a nucleic acid/polycation complex prior to or after formation of the complex.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Condensing a polymer means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism.

Substructure means the chemical structure of the compound and any compounds derived from that chemical structure from the replacement of one or more hydrogen atoms by any other atom or change in oxidation state. For example if the substructure is succinic anhydride, then methylsuccinic anhydride, 2,2-dimethylsuccinic anhydride, 3-oxabicyclo [3.1.0]hexane-2,4-dione, maleic anhydride, citriconic anhydride, and 2,3-dimethylmaleic anhydride have the same substructure.

Succinylated (Succinylation) means the compound obtained from the chemical reaction of the amine with succinic anhydride. For example, succinylated poly-L-lysine means the product from the chemical reaction between poly-L-lysine and succinic anhydride.

A salt is any compound containing ionic bonds, that is bonds in which one or more electrons are transferred completely from one atom to another. Salts are ionic compounds that dissociate into cations and anions when dissolved in solution and thus increase the ionic strength of a solution.

Pharmaceutically acceptable acid addition salts are those salts that retain the biological effectiveness and properties of the free bases, are not biologically or otherwise undesirable, and are formed with inorganic acids such as hydrochloric acid, hydrobromic acis, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethansulfonic acid, p-toluenesulfonic acid, salicylic acid, trifluoroacetic acid, and the like.

Pharmaceutically acceptable base addition salts are those salts that retain the biological effectiveness and properties of the free acids, and are not biologically or otherwise undesirable. These salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

A lipid is any of a diverse group of organic compounds that are insoluble in water, but soluble in organic solvents such as chloroform and benzene. Lipids contain both hydrophobic and hydrophilic sections. Lipids is ment to include complex lipids, simple lipids, and synthetic lipids. Complex lipids are the esters of fatty acids and include glycerides (fats and oils), glycolipids, phospholipids, and waxes. Simple lipids include steroids and terpenes. Synthetic lipids includes amides prepaired from fatty acids wherin the carboxylic acid has been converted to the amide, synthetic variants of complex lipids in which one or more oxygen atoms has been substituted by another heteroatom (such as Nitrogen or Sulfur), and derivatives of simple lipids in which additional hydrophilic groups have been chemically attached. Synthetic lipids may contain one or more labile group.

Glycolipids are sugar containing lipids. The sugars are typically galactose, glucose or inositol. Phospolipids are lipids having both a phosphate group and one or more fatty acids (as esters of the fatty acid). The phosphate group may be bound to one or more additional organic groups.

Fats are glycerol esters of long-chain carboxylic acids. Hydrolysis of fats yields glycerol and a carboxylic acid—a fatty acid. Fatty acids may be saturated or unsaturated (contain one or more double bonds). Fatty acids are considered the hydrolysis product of lipids (fats, waxes, and phosphoglycerides).

Oils are esters of carboxylic acids or are glycerides of fatty acids. Waxes are any of various solid or semisolid substances generally being esters of fatty acids.

Hydrophobic groups indicate in qualitative terms that the chemical moiety is water-avoiding. Typically, such chemical groups are not water soluble, and tend not to form hydrogen bonds.

Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

The examples describe properties of polyion/polyampholyte complexes when polyampholyte is formed in the presence of polyion. Example 1 represents general procedures for the synthesis of PLL-SPLL polyampholyte in the presence of DNA using water-soluble carbodiimide. Example 2 teaches that the formation of PLL-SPLL polyampholyte in the presence of DNA increases the colloid stability of the DNA complex in physiological salt solutions. Example 3 states that the net charge of cross-linked DNA/PLL/SPLL stays negative. Example 4 demonstrates enhanced colloid stability of DNA/polyampholyte complex in the presence of serum. Example 5 teaches about delivery of DNA/PLL-SPLL polyampholyte complex to hepatocytes in vivo. Example 6 is about the same with DNA/ polyallylamine-cysteine-polyacrylic acid-thioester polyampholyte.

EXAMPLE 1

General Procedure for the Formation of the Polyampholyte in the Presence of DNA

Crosslinking of polycation and polyanion layers on the DNA/PLL/SPLL particles using 1[3-(dimethylamino)propyl]-3-ethyl carbodiimide (EDC) and sulfo-N-hydroxysuccinmide (SNHS). Plasmid DNA (pCILuc) and PLL (M. w. 46 kDa) were mixed in a charge ratio 1:3 (100 ug and 190 ug respectively in 0.5 ml of 20 mM MES, pH 6.5. Succinylated PLL (SPLL) was activated with EDC/SNHS in 50 ul of unbuffered solution at pH 5.0 for 10 min (690 ug SPLL, 1.4 mg EDC, 700 ug SNHS). Then the DNA/PLL complex and activated SPLL were mixed (DNA:PLL:SPLL charge ratio 1:3:10) and the mixture was incubated overnight at room temperature.

EXAMPLE 2

Formation of PLL-SPLL Polyampholyte in the Presence of DNA Increases the Colloid Stability in Physiological Salt Solutions In this example the colloid stability of DNA/polyampholyte particles obtained in Example 1 and control DNA/PLL/SPLL complexes were compared using quasielastic light scattering. Control DNA/PLL/SPLL complexes were prepared using the same charge ratios (1:3:10) as DNA/polyampholyte complex in Example 1 but without EDC/SNHS activation (no polyampholyte was formed). The complexes were sized in 10 mM HEPES, pH 7.5 or HEPES buffered saline (20 ug DNA/ml) using Zeta Plus Particle Size Analyzer (Brookhaven Instruments Corp.). Polyampholyte complexes demonstrate more resistance to aggregation in NaCl-containing solutions as compared to control non-covalent complexes (FIG. 1, XL stands for cross-linking).

EXAMPLE 3

Figure 2:
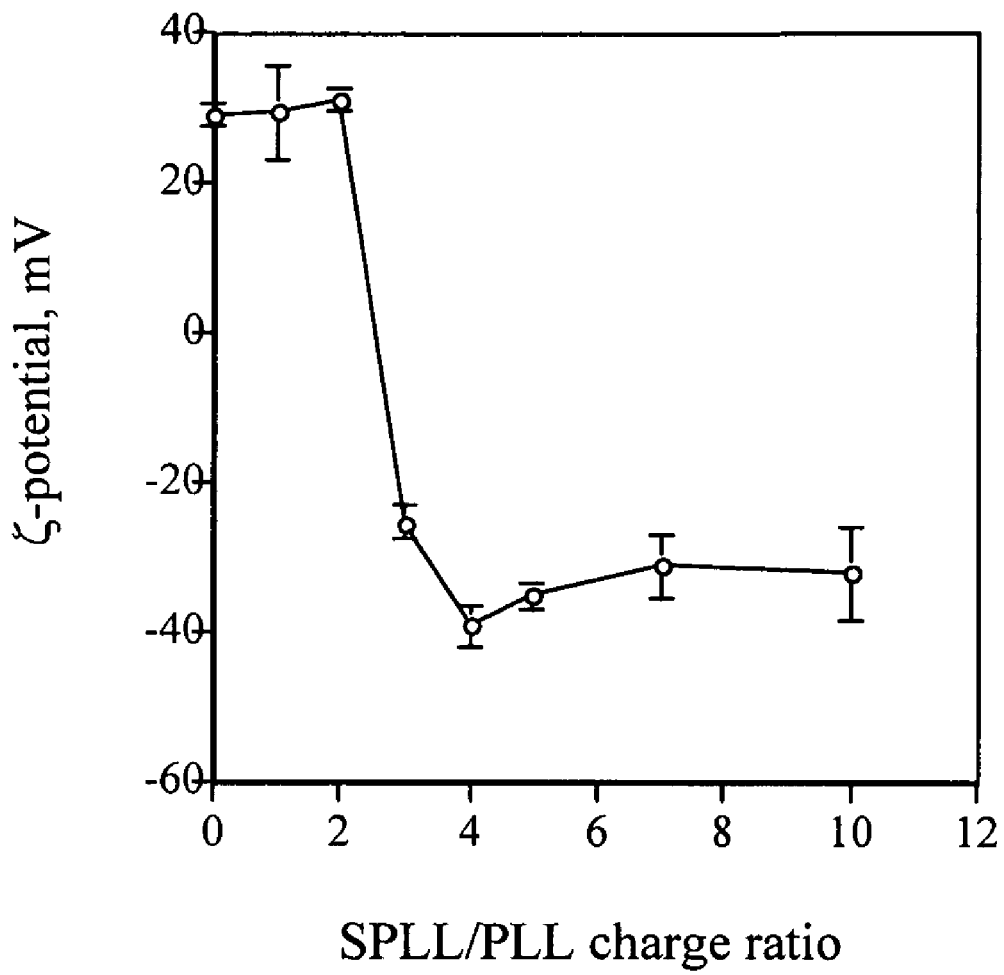
FIG. 2. Illustration of the effect of varying amounts of SPLL polyanion on the surface charge of DNA/PLL complexes.

Surface Charge of DNA Complexes Obtained by Formation of PLL-SPLL Polyampholyte in the Presence of DNA The series of complexes were prepared as described in Example 1 except various amounts of activated SPLL were added to DNA/PLL (1:3) complex. Zeta potential was measured in 10 mM HEPES, pH 7.5 at DNA concentration of 20 ug/ml using Zeta Plus instrument. The results clearly indicate charge reversal when sufficient amounts of activated SPLL are added to form polyampholyte (FIG. 2).

EXAMPLE 4

Crosslinking of Polycation and Polyanion Layers on the DNA-Containing Particles Increases their Stability in Serum and on the Cell Surface Negatively charged (recharged) particles of condensed DNA can possess the same physico-chemical properties as positively charged (non-recharged) ones. This includes flocculation in high salt solutions (including physiologic concentration). We found that chemical cross-linking of cationic and anionic layers of the DNA particles can substantially improve stability of the particles in serum as well as on the cell surface. Table 2 shows the time course of unimodal particle size of DNA/PLL/SPLL crosslinked and non-crosslinked particles in 80% bovine serum as determined by dynamic light scattering.

TABLE 2

Particle sizing of DNA/PLL/SPLL crosslinked and non-crosslinked complexes in 80% serum.

| time (min) | size (nm) no crosslinking | size (nm) crosslinking |
|---|---|---|
| 0 | 153 | 104 |
| 15 | 154 | 105 |
| 60 | 171 | 108 |
| 200 | 246 | 115 |

Crosslinked particles essentially do not change their size in 200 min at room temperature while non-crosslinked control flocculates rapidly. Crosslinking with cleavable reagents might help to overcome an inactivity problem. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

EXAMPLE 5

Hepatocyte Delivery of Cross-Linked Tertiary DNA/PLL/SPLL Complexes by Tail Vein Injection Plasmid DNA (pCILuc) was labeled with Cy3 LableIT (Mirus Corporation, Madison Wis.). Labeled DNA were typically dissolved in water at concentrations ranged from 1.5-2 mg/ml. Poly-L-Lysine, PLL (MW 31 kDa), dissolved in water at 10 mg/ml was purchased from Sigma Chemicals (St. Louis, Mo.). Succinylated PLL (SPLL) was prepared as previously described and dissolved in water at 20 mg/ml. DNA/PLL/SPLL cross-linked tertiary complexes were formed at a charge ratio of 1:3:10 as follows for a single injection: SPLL (345 µg in 50 µl of 20 mM MES, pH 5) were activated with the addition of 292 µg of 5 EDC followed by 583 µg of sulfo-NHS, both were dissolved in $H_2O$ at 100 mg/1.2 ml, and incubated for 10 min. At the end of the activation period, 50 µg of cy3-labeled DNA in 100 µl of 20 mM MES, pH 6.5 was added to 95 µg of PLL in 100 µl of 20 mM MES, pH 6.5 and mixed immediately. The condensed DNA/PLL complexes were added immediately to the activated SPLL solution and mixed thoroughly. The cross-linked particles were allowed to incubate at room temperature for at least 2 hr before in-vivo injections. Typically, a majority of the particles size ranged from 60-200 nm with an average size around 130 nm and a ζ-potential of −40 mV. Salt and serum stability of particles were evaluated by particles size changes over time in the presence of physiologic salt solution or serum. The cross-linked particles solution containing 50 µg of Cy3-DNA in 250 µl were injected into a mouse through the tail vein. After 3 hrs, the animal was sacrificed, liver samples were submerged in HistoPrep (Fisher Scientific) and snapped frozen in liquid nitrogen. Frozen liver sections, 4-5 µm thick, were prepared and were counter stained sequentially for 20 min each by 10 nm Sytox green (Molecular Probe) in PBS for cell nuclei and 15 ng/ml of Alexa 488 phalloidin (Molecular Probe) in PBS for actin filaments. Stained slides were analyzed for hepatocytes uptake of Cy3-DNA containing particles using a Zeiss laser scanning confocal microscope. Hepatocytes were distinguishable by their larger size in comparison to other cells and bi-nucleated for a large percentage of the population. A large number of particles were also found in Kuppfer and endothelial cells.

EXAMPLE 6

Hepatocyte Delivery of DNA/Polyallylamine-Cysteine/Polyacrylic Acid-Thioester Complexes A. Synthesis of polyallylamine-cysteine (pAllylamine-cys) conjugate: N,N'-bis(t-BOC)-L-cystine (37 mg, 0.08 mmol) was dissolved in 5 mL methylene chloride. To this was added N-hydroxysuccinimide (21 mg, 2.2 eq) and dicyclohexylcarbodiimide (37 mg, 2.2 eq). The solution was allowed to stir overnight at room temperature. The dicyclohexylurea was removed by filtering the solution through a cotton plug in a Pasteur pipette. The succinimidyl ester was then added, with rapid stirring, to a solution of polyallylamine hydrochloride MW 50,000 (10 mg, 0.8 eq) that had been dissolved in a solution of methanol (20 mL) and 15 diisopropylethylamine (0.5 mL). After one hour, the solvents were removed by rotary evaporation. The white solid was then dissolved in trifluoroacetic acid (5 mL), triisopropylsilane (0.25 mL), and water (0.25 mL). After two hours, the solvents were removed by rotary evaporation. The resulting solid was then dissolved in water (25 mL) and the pH was adjusted to 9 by the addition of potassium carbonate. To this solution was added β-mercaptoethanol (1 mL). After two hours, the pH was adjusted to 2 by the addition of hydrochloride and the solution was placed into dialysis tubing (MWC 12,000) and dialyzed against 2 L of water that was adjusted to pH 2 with addition of hydrochloric acid. The dialysis solution was changed four times over 48 hours. After dialysis the solution contained 1.3 mg/mL polyallylamine, which is 14 mM of amine functional groups. Analysis of the thiol content of the solution by reaction with 5,5'-dithiobis(2-nitrobenzoic acid) in pH 7.5 100 mM phosphate buffer and quantification by comparison to solutions containing a known amount of β-mercaptoethanol revealed 2.7 mM of thiol functional groups, an 18% modification of all functional groups.

B. Synthesis of polyacrylic acid thioester (pAA-thioester): To a solution of mercaptoacetic acid (1 mL) in 10 mL methylene chloride was added polyacryloyl chloride MW 10,000 (100 mg). After 30 minutes, the methylene chloride was removed by rotary evaporation and the resulting oil was dissolved in 20 mL water and dialyzed against 2 L water. The dialysis solution was changed four times over a 72 hour period. The amount of thioester was quantified by measuring the absorbance of the thioester at 230 nm using the extinction coefficient of 3,800 $M^{-1}cm^{-1}$ (Anal. Biochem. 1985, 150, 121) and was determined to be at 80% modification of all functional groups. Complexes for injection were formulated in 250 µl of 5 mM HEPES buffer, pH 8. For a single injection, 20 µg of pAllylamine-cys was added to 10 µg of Cy3-DNA. Polyacrylic acid thioester (60 ug) was then added to the condensed complex and let incubate overnight at 4° C.

C. Amide bonds were formed as interactions occurred between the cysteine groups and the thioester groups. These cross-linked particles had an average diameter of 94 nm in size and a δ-potential of −40 mV. Particle stability were evaluated by changes of particles size in the presence of physiologic salt and serum. Injection of complexes and analysis for hepatocyte delivery were essentially the same as described in example 1. Complexes were observed in at least 60% of the hepatocytes. Considering the lower concentration of DNA injected, the efficiency of hepatocytes delivery was comparable to that of Cy3-DNA/PLL/SPLL complexes. Similar to Cy3-DNA/PLL/SPLL complexes, sinusoidal cells (mostly endothelial and Kupffer cells) also contained a large number of particles. This example represent another method of cross-linking to formulate liver targetable negatively charged particles.

EXAMPLE 7

Synthesis of Amine-Containing Polyvinyl Ethers

2-Vinyloxy Ethyl Phathalimide was added to a oven dried round bottom flask under a blanket of nitrogen in anhydrous dichloromethane to this solution was added ethyl vinyl ether, propyl vinyl ether, or butyl vinyl ether. These solutions were then brought to −78° C. and BF$_3$.OEt$_2$ (0.1 molar equivalents relative to total vinyl ether) is added and the reaction is allowed to proceed for 2 hours at −78° C. The polymerization is then stopped by the addition of 50/50 mixture of ammonium hydroxide in methanol. The solvents are then removed by rotary evaporation. To remove the phthalimide protecting group, the polymer is then dissolved in 30 mL of 1,4-dioxane/methanol (2/1). To this solution was added hydrazine (10 molar equivalents) and the mixture was heated to reflux for 3 hours. The solvents are then removed by rotary evaporation and the resulting solid was then brought up in 20 mL of 0.5M HCl and refluxed for 15 minutes, diluted with 20 mL distilled water, and refluxed for additional hour. This solution was then neutralized with NaOH cooled to room temperature and transfer to 3,500 molecular cellulose tubing and dialyzed for 24 h (2×20 L) against distilled water, and freeze dried.

Lyophilized polymer was dissolved in water. 5 mL aliquots were placed onto a 2.5×20 cm column packed with Sephacryl S-200. The column was eluted with 25 mM (NH$_4$)$_2$CO$_3$ 5% ethanol and 10 mL fractions were collected after dead volume (25 mL). Fractions were then assayed by trinitrobenzenesulfonic acid for amine content. Four equal fractions were then pooled and lyophilized. The first fraction, with an approximate molecular weight >10,000, was used for in vivo tracking assays.

EXAMPLE 8

PEG Modification of Polyvinyl Ether

Polyvinyl ethers as described above were modified with N-hydroxysuccinimide esters of polyethylethylene glycol (NHS-PEG from Nektar) at 0.2-1.0 weight equivalents. 0.01 weight equivalents of PEG groups also have a terminal biotin group (Nektar). The modified polyvinyether is then isolated by size exclusion chromatography using Sephacryl S-200.

Using these procedures, polymer DW872 was synthesized from a 1:1 molar feed ratio mixture of phthalimido and butyl vinyl ethers. After size exclusion chromatography, it was modified with 0.45 weight equivalents of NHS-PEG (MW 5000) and 0.05 weight equivalents of NHS-PEG-biotin. Similarly, polymer DW863 was synthesized from a 1:1 NH$_2$:butyl feed ratio followed by modification with 20 weight percent PEG.

EXAMPLE 9

Synthesis of CDM-PEG Derivatives

To a solution of 2-propionic-3-methylmaleic anhydride (30 mg, 0.16 mmol) in 5 mL methylene chloride was added oxalyl chloride (200 mg, 10 eq) and dimethylformamide (1 µL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added 2 equivalents polyethylene glycol monomethyl ether of various molecular weights, and pyridine (20 µL, 1.5 eq) in 10 mL of methylene chloride. The solution was then stirred for 2 hours. By this synthetic procedure, the propionic acid group reacts with the alcohol group of polyethylene glycol to form an ester. Similarly, an amine group at the end of amino polyethylene glycol could be reacted with the propionic acid group of CDM to from an amide. The solvent was then removed and the resulting solid was dissolved into 5 mL of water and purified using reverse-phase HPLC using a 0.1% TFA water/acetonitrile gradient.

EXAMPLE 10

DNA Labeling

Covalent labeling of plasmid DNA with fluorophores was performed using tetramethylrhodamine (TMR) or Oregon Green (OG) LabelIT reagent (Mirus Corp., Madison, Wis.) according to the manufacturer's recommendations. Briefly, plasmid DNA and a solution of LabelIT reagent in methyl sulfoxide (100 mg/ml) were mixed in 1 ml of 10 mM HEPES, pH 7.5 at a reagent/DNA ratio of 5:1 (w/w). The reaction mixture was incubated for 1 h at 37° C. Labeled DNA was then precipitated three times in 70% ethanol with 0.2 M NaCl.

EXAMPLE 11

DNA Condensation Assay

The collapse of TMR-labeled DNA was assessed using a quantitative assay based on condensation-induced quenching of a fluorophore covalently attached to DNA. Briefly, TMR-DNA (10 µg) was mixed with various quantities of polyvinyl ethers or melittin in 0.5 ml of 10 mM HEPES, pH 7.5. Rhodamine fluorescence of the samples was measured using a Varian spectrofluorometer (excitation wavelength ($\lambda_{ex}$) of 546 nm; emission wavelength ($\lambda_{em}$) of 576 nm) at room temperature. Similarly, DNA condensation may be assayed using OG label ($\lambda_{ex}$=495 and $\lambda_{em}$=525).

EXAMPLE 12

Synthesis of Disulfide-Containing Dialdehyde 1-thioglycerol was oxidized to a disulfide by addition of iodine in methylene chloride until the purple iodine color remained. The disulfide was then precipitated from solution by addition of 10 volume equivalents of diethylether and incubation at −78° C. for a week. The resulting disulfide was then oxidized in water by the addition of 12 weight equivalents of sodium periodate. After 3 hours of oxidation, the dialdehyde solution was used.

EXAMPLE 13

Crosslinking DNA-Condensed Particle by Addition of Disulfide-Containing Dialdehyde 10 µg/mL tetramethylrhodamine labeled DNA in 5 mM HEPES pH8.0 isotonic glucose was condensed with 20 µg/mL PLL. To the particles was then added 0, 1, 2, 3, 4, 5, 6, 7, 8, 9, or 10 µg/mL disulfide-containing dialdehyde. After 2 hour, 150 mM NaCl and 100 µg/mL polyacrylic acid 15 kDa was added. Fluorescence was then measured and normalized to flourescence of uncondensed DNA. Each data point is the average of duplicates.

| disulfide dialdehyde added (µg/mL) | Percent release of DNA (relative to DNA alone) |
|---|---|
| 0 | 97 |
| 1 | 69 |

-continued

| disulfide dialdehyde added (μg/mL) | Percent release of DNA (relative to DNA alone) |
|---|---|
| 2 | 40 |
| 3 | 26 |
| 4 | 16 |
| 5 | 15 |
| 6 | 14 |
| 7 | 14 |
| 8 | 13 |
| 9 | 13 |
| 10 | 16 |

EXAMPLE 14

Crosslinking DNA-Condensed Particle by Addition of Glutaraldehyde

10 μg/mL Oregon Green labeled DNA in 5 mM HEPES pH8.0 isotonic glucose was condensed with 60 μg/mL DW765 (synthesized from 1:1 molar mixture of putative-$NH_2$ and propyl vinyl ethers and modified with 15 wt. % PEG5000). To the particles was then added 0, 3, 6, 7.5, 15, or 30 μg/mL glutaraldehyde. After 2 hour, 150 mM NaCl and 200 μg/mL polyacrylic acid 15 k was added. The fluorescence was then measured and normalized to flourescence of uncondensed DNA. Each data point is the average of duplicates.

| weight equilavents of glutaraldehyde | Percent release of DNA (relative to DNA alone) |
|---|---|
| 0.000 | 78 |
| 0.050 | 66 |
| 0.100 | 53 |
| 0.125 | 41 |
| 0.250 | 23 |
| 0.500 | 5 |

EXAMPLE 15

Modification of Glutaraldehyde-Crosslinked Particle Charge.

Polymer DW863 was added to DNA at a weight ratio of 1:10 in 400 μl of 5 mM HEPES, pH 8, 290 mM glucose. Complexes were crosslinked for 3 hr at room temperature with 12.5 μg glutaraldehyde (relative to DW863). The resultant caged DNA:DW863 particles were modified with 0, 5, 10, 15, or 20 weight percent (relative to polymer) sulfo-NHS-acetate (Pierce Biotechnology, Rockford, Ill.) or 3 wt equivalents of CDM-PEG (MW=430). The zeta potential was then measured using a Brookhaven Zeta Plus with ZetaPALS. An average of ten measurements is reported.

| Formulation | Zeta potential (mV) |
|---|---|
| No crosslinking | 16.3 |
| 12.5 wt % glutaraldehyde, no acylation | 13.8 |
| 5 wt % acylation reagent | 9.7 |
| 10 wt % acylation reagent | 8.4 |
| 15 wt % acylation reagent | 7.4 |
| 20 wt % acylation reagent | 4.9 |
| 3 weight eq. CDM-PEG | 2.7 |

EXAMPLE 16

Chemical Neutralization of Disulfide-Containing Dialdehyde-Crosslinked Particles Polymer DW863 was added to DNA at a weight ratio of 1:10 in 400 μl of 5 mM HEPES, pH 8, 290 mM glucose. Complexes were crosslinked for 3 hr at room temperature with 0.8 weight equivalents of disulfide-containing dialdehyde. The resultant caged DNA:DW863 complexes were modified with 0 or 20 weight percent (relative to polymer) sulfo-NHS-acetate (Pierce Biotechnology, Rockford, Ill.) or 3 wt equivalents of CDM-PEG(MW=430). The zeta potential was then measured using a Brookhaven Zeta Plus with ZetaPALS. An average of three measurements is reported.

| Formulation | Zeta potential (mV) |
|---|---|
| No acylation | 6.3 |
| 20 wt % | −1.5 |

EXAMPLE 17

Preparation of T7-Peptide Streptavidin (SA) Conjugates

Two mg of SA (Jackson ImmunoResearch Laboratories, West Grove, Pa.) was dissolved in 200 μl of $dH_2O$ and added to a 200 μl solution of 100 mM sodium phosphate, 300 mM NaCl, 2 mM EDTA, pH 7.2. A 20 mole equivalent of SPDP (Pierce) dissolved in DMF at 10 mg/ml was then added to the SA solution and mixed at RT for 1 hr. The SPSP-modified streptavidin was then purified using a G-25 Sephadex column. Typically SA molecule contained an average of 6-8 PDP groups based on a pyridine-2-thione assay. The SA-PDP conjugate was added to MC920 (a liver targeting T7-peptide) or MC993 (a non-targeting T7-peptide) at a 1:3 molar ratio and incubated for 24 hr at 4 C. The MC920-SA and MC993-SA conjugates were then purified on a G-25 Sephadex column. The sample was then freeze-dried and dissolved in a solution of 25 mM MES, 125 mM NaCl, pH 6.5 at 3 mg/ml. The targeting functions of the conjugates were confirmed by delivery of biotinylated molecules.

EXAMPLE 18

The In Vivo Hepatocyte Targeting of Condensed DNA Particles

To demonstrate the dependence of targeting on the crosslinking and charge (zeta potential) of the particles we made three formations: a) no crosslinking, b) crosslinking with glutaraldehyde, c) crosslinking with glutaraldehyde plus charge neutralization. Cationic Polymer DW872 was added to Cy3-DNA at a weight ratio of 1:10 in 400 μl of 5 mM HEPES, pH 8, 290 mM glucose. DNA condensation was verified by fluorescence quenching. Complexes were crosslinked for 3 hr at room temperature with 12.5 μg glutaraldehyde (relative to DW872). The resultant caged DNA:DW872 complexes were ~55-60 nm in size with approximate zeta potential greater than +10 mV. To reduce the net ζ-potential, the caged complexes were modified with sulfo-NHS-acetate (Pierce Biotechnology, Rockford, Ill.) or CDM-$PEG_{500}$ (2-Propionic-3-Methylmaleic Anhydride-$PEG_{500}$). For modification with sulfo-NHS-acetate, reaction was incubated overnight at room temperature to allow for hydrolysis of excess reagent prior to addition of p17 peptide conjugate (see below). P17 peptide is a hepatocyte targeting ligand. The final ζ-potential for these complexes was less than +10 mV. CDM-PEG$_{500}$ was added to complexes 10 min prior to injection. The ζ-potential of these complexes was also less than +10 mV. 2 equivalents (streptavidin to biotin) of streptavidin-targeting peptide conjugate was then added to each sample. Similarly, we have also conjugated other targeting ligands such as galactose to the crosslinked, acylated particles. For each injection, 20 μg of DNA complexes in 250 μl of the formulation buffer was injected. Liver samples were excised, frozen, and sectioned 1 hr after injection.

Figure 3:
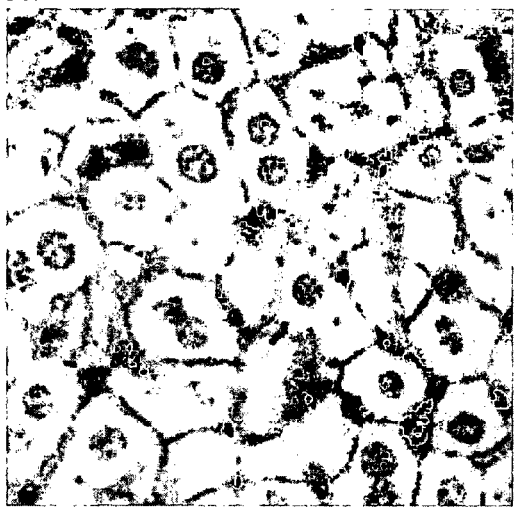
FIG. 3. Illustration of delivery of non-crosslinked complexes, crosslinked complexes, and charge reduced complexes to the liver of mice in vivo.
Figure 3:
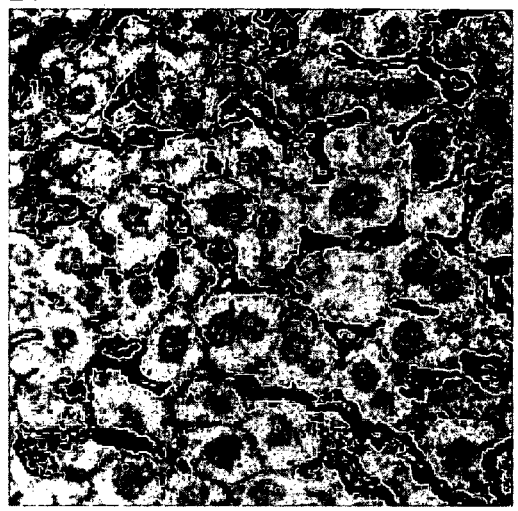
Figure 3:
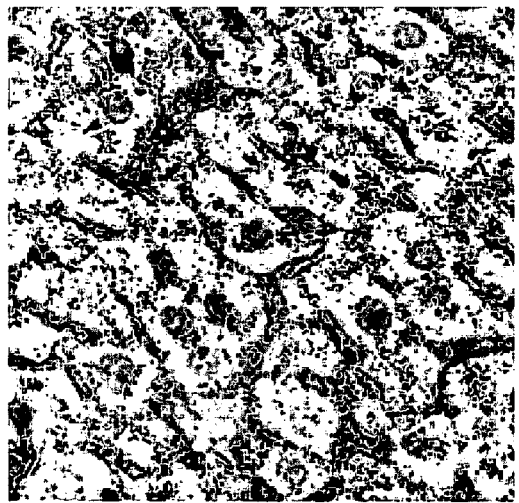

Without any crosslinking, very few of the DNA particles were observed in the liver. Crosslinking the particles enhanced DNA delivery significantly. Chemical charge reduction of the particles, by removal of amine charges, resulted in the highest levels of hepatocyte targeting (FIG. 3).

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a nucleic acid to a cell, comprising:
   a) condensing the nucleic acid with a polycation to form a complex with a positive surface charge;
   b) crosslinking the polycation;
   c) reducing the surface charge of the complex by chemically modifying positively charged moieties on the polycation with a maleic anhydride derivative; and,
   d) contacting the cell with the reduced surface charge complex.

2. The process of claim 1 further comprising modifying the polycation to add a targeting ligand.

3. The process of claim 2 wherein the targeting ligand consists of galactose.

4. The process of claim 1 wherein the maleic anhydride derivative is charge neutral.

5. The process of claim 1 wherein the maleic anhydride derivative negatively charged.

6. The process of claim 1 wherein the maleic anhydride derivative contains an interaction modifier group.

7. The process of claim 6 wherein the interaction modifier group consists of polyethylene glycol.

8. The process of claim 1 wherein the maleic anhydride derivative contains a targeting group.

9. The process of claim 8 wherein the targeting group contains a galactose molecule.

10. The process of claim 1 wherein the maleic anhydride derivative consists of a dimethylmaleic anhydride derivative.

11. The process of claim 1 wherein the maleic anhydride derivative consists of a 2-propionic-3-methylmaleic anhydride.

12. The process of claim 11 wherein the 2-propionic-3-methylmaleic anhydride consists of a 2-propionic-3-methylmaleic anhydride-polyethylene glycol.

13. The process of claim 1 wherein crosslinking the polycation comprises adding a multivalent crosslinker to the complex.

14. The process of claim 13 wherein the crosslinker consists of a labile crosslinker.

15. The process of claim 14 wherein the crosslinker consists of a cleavable crosslinker.

16. The process of claim 15 wherein the cleavable crosslinker consists of a disulfide bond containing crosslinker.

17. The process of claim 16 wherein the disulfide bond containing crosslinker consists of a disulfide bond dialdehyde.

* * * * *